United States Patent [19]
Jacobs et al.

[11] Patent Number: 5,876,531
[45] Date of Patent: Mar. 2, 1999

[54] PROCESS FOR MAKING A MECHANICAL FASTENER HAVING A GRIP TAB

[75] Inventors: Mark Charles Jacobs, Appleton; David Kurth Foth; David Andrae Justmann, both of Hortonville; Lawrence Paul Plaia; Stuart James Burgan, both of Appleton, all of Wis.

[73] Assignee: Kimberly-Clark Worldwide, Inc., Neenah, Wis.

[21] Appl. No.: 603,476

[22] Filed: Mar. 6, 1996

[51] Int. Cl.⁶ ...................................................... A61F 13/16
[52] U.S. Cl. ......................... 156/66; 156/256; 156/264; 156/265; 156/269; 156/271; 604/391
[58] Field of Search ..................... 156/264, 265, 156/271, 269, 256, 66; 604/391

[56] References Cited

U.S. PATENT DOCUMENTS

| | | |
|---|---|---|
| 2,738,789 | 3/1956 | Foxworthy . |
| 2,834,347 | 5/1958 | Connally . |
| 3,089,494 | 5/1963 | Schwartz . |
| 3,221,738 | 12/1965 | Ekberg et al. . |
| 3,620,217 | 11/1971 | Gellert . |
| 3,800,796 | 4/1974 | Jacob . |
| 3,901,236 | 8/1975 | Assarsson et al. . |
| 3,948,258 | 4/1976 | Karami . |
| 3,948,267 | 4/1976 | Karami . |
| 3,950,824 | 4/1976 | Karami . |
| 3,967,624 | 7/1976 | Milnamow . |
| 4,010,753 | 3/1977 | Tritsch . |
| 4,034,752 | 7/1977 | Tritsch . |
| 4,051,853 | 10/1977 | Egan, Jr. . |
| 4,060,085 | 11/1977 | Karami . |
| 4,063,559 | 12/1977 | Tritsch . |
| 4,066,081 | 1/1978 | Schaar . |
| 4,074,716 | 2/1978 | Schaar . |
| 4,076,663 | 2/1978 | Masuda et al. . |
| 4,090,516 | 5/1978 | Schaar . |
| 4,158,363 | 6/1979 | Schaar . |
| 4,186,744 | 2/1980 | Ness . |
| 4,209,016 | 6/1980 | Schaar . |
| 4,237,889 | 12/1980 | Gobran . |
| 4,286,082 | 8/1981 | Tsubakimoto et al. . |
| 4,299,223 | 11/1981 | Cronkrite . |

(List continued on next page.)

FOREIGN PATENT DOCUMENTS

| | | |
|---|---|---|
| 0217032 A3 | 4/1987 | European Pat. Off. . |
| 0264959A2 | 4/1988 | European Pat. Off. . |
| 0 379 850 A1 | 8/1990 | European Pat. Off. . |
| 0233704 B1 | 7/1992 | European Pat. Off. . |
| 1426147 | 3/1974 | United Kingdom . |
| 2 160 586 A | 12/1985 | United Kingdom . |
| 2249469 | 5/1992 | United Kingdom . |
| WO 95/05140 A1 | 2/1995 | WIPO . |

*Primary Examiner*—Jeff H. Aftergut
*Attorney, Agent, or Firm*—Paul Yee

[57] ABSTRACT

A method for forming a plurality of fastener components comprises providing a composite web which includes a web of hook material. The hook material includes a hook base layer which has a longitudinally extending medial section located between first and second, laterally opposed, longitudinally extending side sections of the web of hook material. Each of the side sections has a plurality of hook elements which are integrally formed with the base layer and extend away from a base plane of the hook base layer, and the hook elements are configured to operably engage a selected, cooperating loop material to provide an operative fastening. The medial section has a relatively lower density of the hook elements per unit area, as compared to the side sections. The web of hook material has an extending section of carrier web material attached to extend laterally outboard from each of the side sections of the web of hook material. Each section of carrier web material may have an extending web of panel material attached to extend laterally outboard from each section of carrier web material. At least the web of hook material is divided along a serpentine division line which extends generally longitudinally along the web of hook material, and the composite web is selectively segmented to provide for the plurality of fastener components.

23 Claims, 7 Drawing Sheets

U.S. PATENT DOCUMENTS

| | | |
|---|---|---|
| 4,389,212 | 6/1983 | Tritsch . |
| 4,500,316 | 2/1985 | Damico . |
| 4,556,595 | 12/1985 | Ochi . |
| 4,633,565 | 1/1987 | DeWoskin . |
| 4,655,761 | 4/1987 | Grube et al. . |
| 4,663,220 | 5/1987 | Wisneski et al. . |
| 4,699,823 | 10/1987 | Kellenberger et al. . |
| 4,701,170 | 10/1987 | Wilson et al. . |
| 4,701,176 | 10/1987 | Wilson et al. . |
| 4,704,115 | 11/1987 | Buell . |
| 4,704,116 | 11/1987 | Enloe . |
| 4,743,242 | 5/1988 | Grube et al. . |
| 4,753,646 | 6/1988 | Enloe . |
| 4,753,648 | 6/1988 | Jackson . |
| 4,753,649 | 6/1988 | Pazdernik . |
| 4,773,906 | 9/1988 | Krushel . |
| 4,787,897 | 11/1988 | Torimae et al. . |
| 4,795,510 | 1/1989 | Wittrock et al. . |
| 4,820,296 | 4/1989 | Masliyah . |
| 4,826,499 | 5/1989 | Ahr . |
| 4,834,742 | 5/1989 | Wilson et al. . |
| 4,842,596 | 6/1989 | Kielpikowski et al. . |
| 4,850,988 | 7/1989 | Aledo et al. . |
| 4,883,481 | 11/1989 | Blanchard . |
| 4,887,339 | 12/1989 | Bellanger . |
| 4,894,060 | 1/1990 | Nestegard . |
| 4,895,569 | 1/1990 | Wilson et al. . |
| 4,911,702 | 3/1990 | O'Leary et al. . |
| 4,916,005 | 4/1990 | Lippert et al. . |
| 4,938,753 | 7/1990 | Van Gompel et al. . |
| 4,955,113 | 9/1990 | Rajala et al. . |
| 4,984,339 | 1/1991 | Provost et al. . |
| 5,019,073 | 5/1991 | Roessler et al. . |
| 5,024,672 | 6/1991 | Widlund . |
| 5,040,525 | 8/1991 | Georgijevic . |
| 5,092,862 | 3/1992 | Muckenfuhs et al. . |
| 5,141,790 | 8/1992 | Calhoun et al. . |
| 5,147,347 | 9/1992 | Huang et al. . |
| 5,158,557 | 10/1992 | Noreen et al. . |
| 5,170,505 | 12/1992 | Rohrer . |
| 5,226,992 | 7/1993 | Morman . |
| 5,242,436 | 9/1993 | Weil et al. . |
| 5,269,776 | 12/1993 | Lancaster et al. . |
| 5,279,604 | 1/1994 | Robertson et al. . |
| 5,288,546 | 2/1994 | Koessler et al. ............... 604/391 X |
| 5,399,219 | 3/1995 | Roessler et al. . |
| 5,407,439 | 4/1995 | Goulait . |
| 5,482,588 | 1/1996 | Goulait et al. .................. 156/264 |
| 5,487,809 | 1/1996 | Goulait et al. . |
| 5,549,592 | 8/1996 | Fries et al. ..................... 604/391 X |

# 5,876,531

PROCESS FOR MAKING A MECHANICAL FASTENER HAVING A GRIP TAB

FIELD OF THE INVENTION

The present invention relates to a technique for forming a fastening system. More particularly, the invention relates to a technique for forming an article having a side panel member connected to a fastening system which incorporates a distinctive grip tab.

BACKGROUND OF THE INVENTION

Conventional absorbent articles, such as disposable diapers, have been constructed with elasticized waistbands. Particular article designs have incorporated a stretchable outer cover composed of an elastomeric web material, such as a stretch bonded laminate which includes a layer of nonwoven fabric. Other conventional designs have included elastomeric or nonelastomeric side panel members connected to the lateral side edges of an outercover composed of a polymer film material, and fasteners and fastening tabs have been connected to the side panels for securing the article on a wearer. The fastener tabs can include mechanical fastening mechanisms, such as the complementary components of a hook-and-loop fastener.

Conventional techniques for forming articles which have fastening systems with panel members, however, have exhibited significant shortcomings when incorporated into high speed manufacturing operations. For example, it has been difficult to provide a technique for reliably and efficiently producing a mechanical fastener tab which is easy to open and is also resistant to undesired, premature opening. As a result, there has been a continued need for an improved manufacturing technique which can more effectively produce an article having a more reliable fastening system.

BRIEF DESCRIPTION OF THE INVENTION

A process aspect of the invention provides a method for forming fasteners. The method includes providing a composite web which includes a web of a first mechanical fastening component. The first mechanical fastening component includes a base layer which has a longitudinally extending medial section located between first and second, laterally opposed, longitudinally extending side sections of the first mechanical fastening component web. Each of the side sections has a plurality of first mechanical fastening elements which are integrally formed with the base layer and extend away from a base plane of the base layer, and the first mechanical fastening elements are configured to operably engage a selected, cooperating second mechanical fastening component. The medial section has a relatively lower density of the first mechanical fastening elements per unit area, as compared to the side sections. The web of the first mechanical fastening component has an extending section of carrier web material attached to extend laterally outboard from each of the side sections of the first mechanical fastening component web. At least the web of the first mechanical fastening component is divided along a serpentine division line which extends generally longitudinally along the web of hook material. In particular aspects of the invention, an extending web of panel material has been attached to extend laterally outboard from each section of carrier web material, and in other aspects, the composite web may be selectively segmented to provide for the plurality of fastener components.

The various aspects of the invention can advantageously provide an improved technique for forming a fastener system in which a fastener tab can provide a desired ease of opening while also providing a secure closure which is resistant to undesired, premature pop-opens. With the technique, the fastening system can be manufactured at high speed, and the resultant fastener tab can be more effectively and efficiently provided with a grip tab portion which is less liable to catch or snag on surrounding objects. As a result, the present invention, in its various configurations, can provide an improved technique for forming an article having a more effective and reliable fastening system. The resultant article and fastening system can have more consistent quality and can provide more dependable performance.

BRIEF DESCRIPTION OF THE DRAWINGS

The invention will be more fully understood and further advantages will become apparent when reference is made to the following detailed description and accompanying drawings in which.

DETAILED DESCRIPTION OF THE INVENTION

The method and apparatus of the present invention will be described herein in relationship to their use in producing a fastener system for absorbent articles, particularly disposable absorbent articles. Such articles can be placed against or in proximity to the body of a wearer to absorb and contain various exudates discharged from the body, and are intended to be discarded after a limited period of use. The articles are not intended to be laundered or otherwise restored for re-use. While the present description will particularly be made in the context of a diaper article, it should be understood that the present invention is also applicable to other articles, such as caps, gowns, drapes, covers, adult incontinence garments, sanitary napkins, children's training pants, and the like.

In particular arrangements, the present invention can advantageously be employed to more efficiently produce a fastening system for incorporation into an absorbent article, such as a disposable diaper having a front waistband section, a rear waistband section and an intermediate section which interconnects the front and rear waistband sections. The article includes a backsheet layer, and a liquid permeable topsheet layer which is superposed on the backsheet layer. An absorbent body is located between the backsheet layer and the topsheet layer, and a fastening system is connected to the article at each laterally opposed end region of at least one of the front and rear waistband sections. Each fastening system can include a side panel member, and the side panels can optionally be constructed to be elastomerically stretchable at least along a lateral, cross-direction of the article. A fastening tab for securing the article on a wearer is connected to each of the side panels.

Articles which include elastomeric side panels and selectively configured fastener tabs are described in U.S. patent application Ser. No. 168,615 of T. Roessler et al., entitled DYNAMIC FITTING DIAPER, and filed Dec. 16, 1993 (attorney docket No. 10,961); and in U.S. patent application Ser. No. 603,477 of A. Long et al., entitled MECHANICAL FASTENING SYSTEM WITH GRIP TAB, and filed Mar. 6, 1996 (attorney docket No. 12,563). Various techniques for forming the fastening systems are described in U.S. Pat. No. 5,399,219 of T. Roessler et al., entitled METHOD FOR MAKING A FASTENING SYSTEM FOR A DYNAMIC FITTING DIAPER and issued Mar. 21, 1995 (attorney docket No. 11,186); in U.S. patent application Ser. No. 286,086 of D. Fries, entitled A PROCESS FOR ASSEMBLING ELASTICIZED EAR PORTIONS and filed Aug. 3, 1994 (attorney docket No. 11,169); and in U.S. patent application Ser. No. 08/415,383 of D. Fries et al., entitled AN ASSEMBLY PROCESS FOR A LAMINATED TAPE and filed Apr. 3, 1995 (attorney docket No. 11,950). The entire disclosures of the above-mentioned documents are incorporated herein by reference in a manner that is consistent (not in conflict) herewith.

Figure 1:
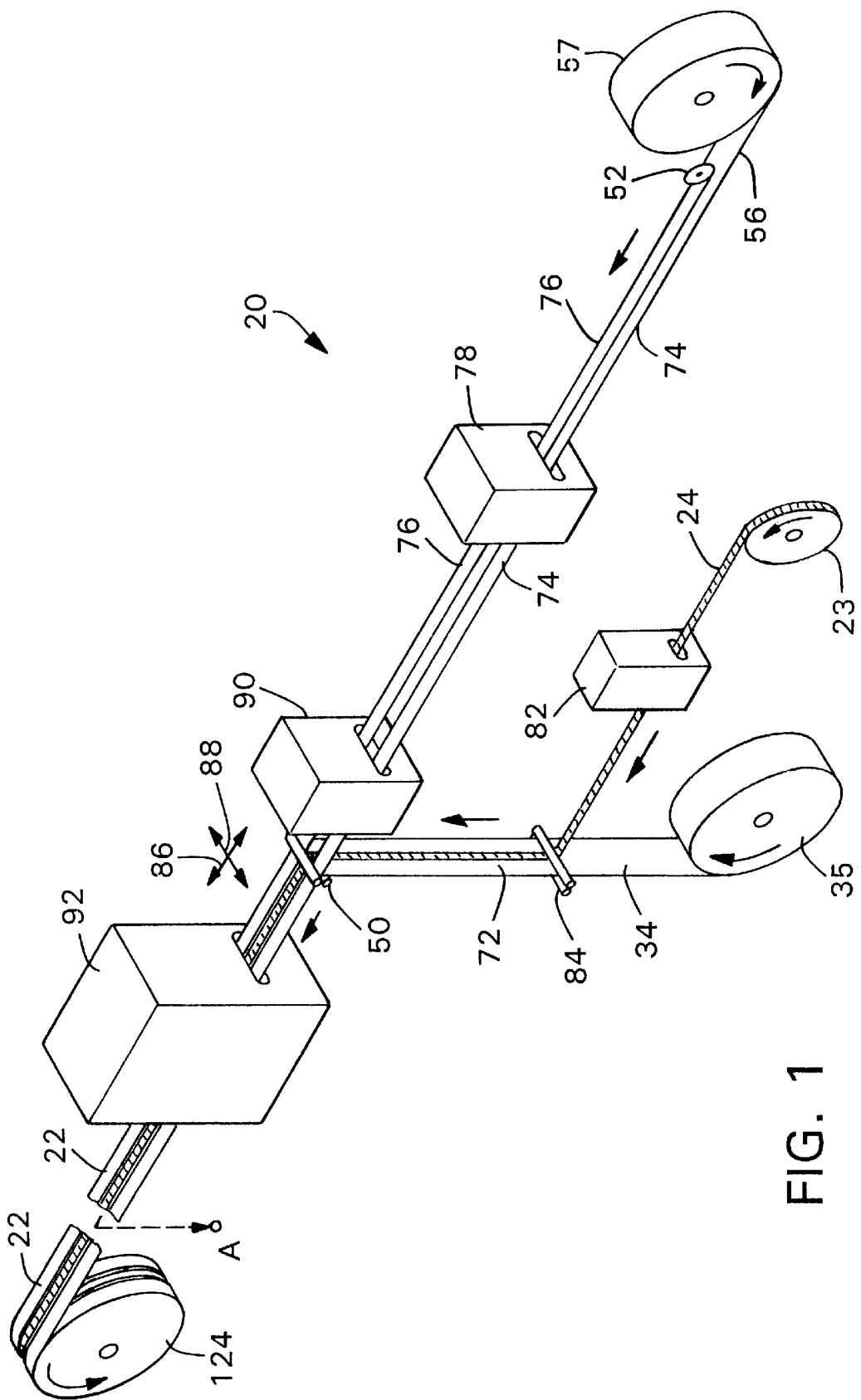
FIG. 1 representatively shows a schematic, perspective view of a portion of the method and apparatus of the invention.
Figure 2:
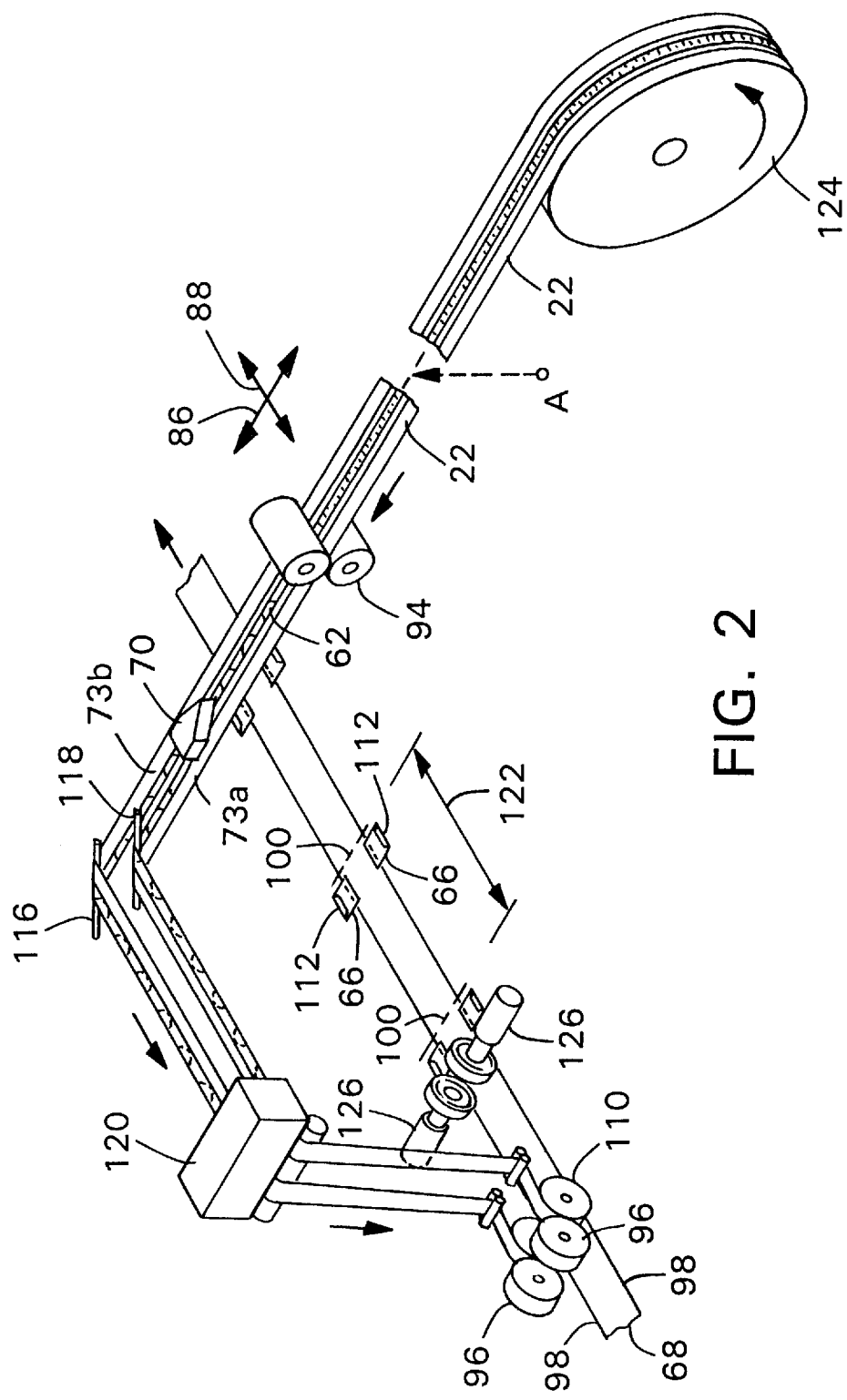
FIG. 2 a schematic, perspective view of another portion of the method and apparatus of the invention.
Figure 3:
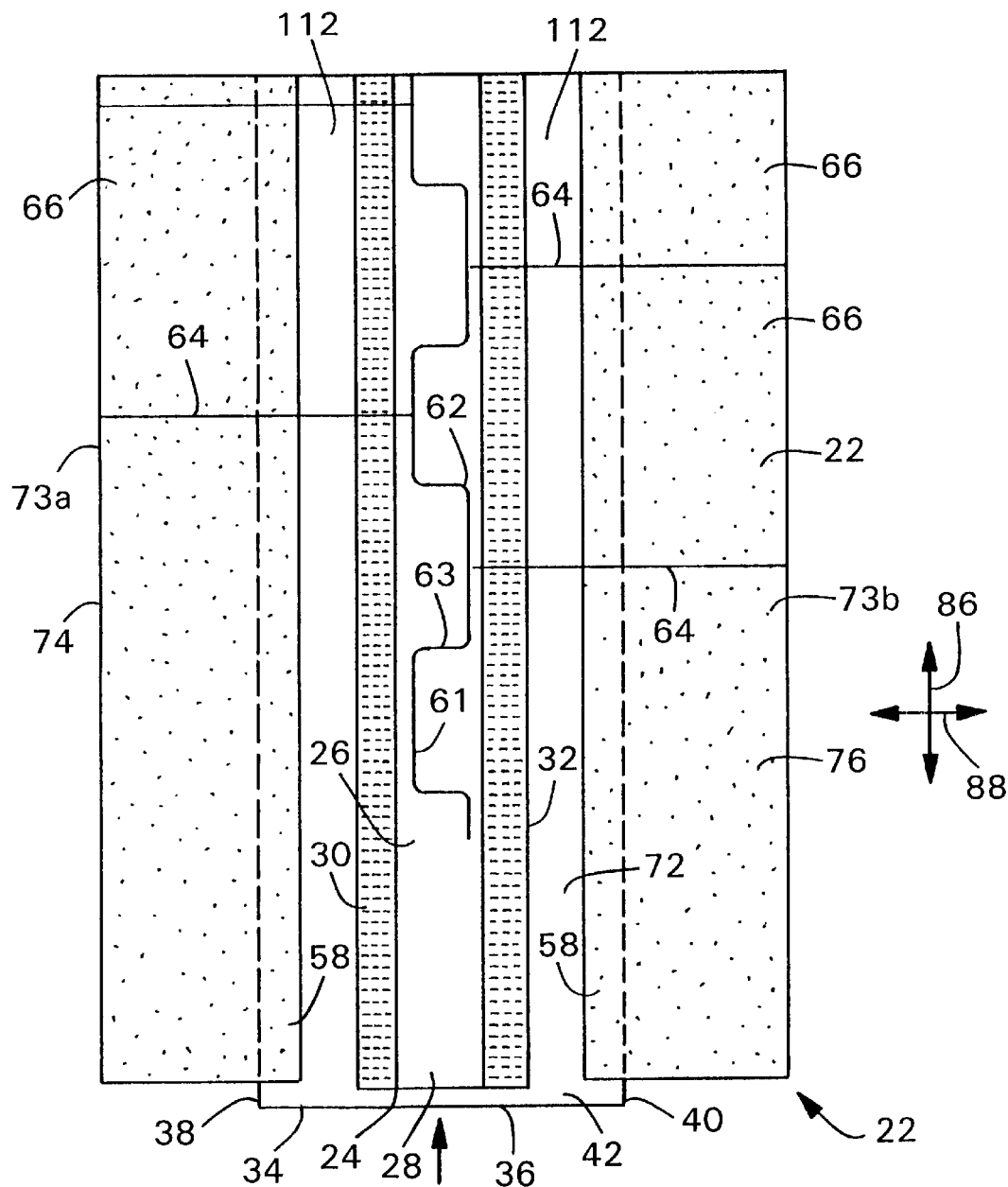
FIG. 3 representatively shows a schematic composite web and its associated components.
Figure 4:
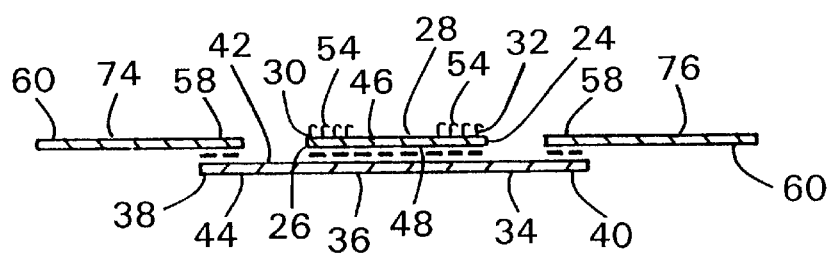
FIG. 4 representatively shows an expanded, schematic cross-sectional, lateral end view of the composite web illustrated in FIG. 3.

The present invention can provide a distinctive technique for forming a fastener system having a selected, composite fastener component. The invention can further provide a distinctive technique for forming a selected article, such as an elasticized disposable diaper which includes a fastening system. With reference to FIGS. 1, 2 and 3, a method and apparatus of the invention, shown generally at 20, for forming a plurality of fastener components 66 includes a providing of a composite web 22 which includes a web of a first mechanical fastening component, such as a web of hook material 24. The first mechanical fastening component web includes a base layer, such as hook base layer 26, which has a longitudinally extending medial section 28 located between first and second, laterally opposed, longitudinally extending side sections 30 and 32 of the first mechanical fastening component web. Each of the side sections 30 and 32 has a plurality of mechanical fastening elements, such as hook elements 54, which are integrally formed with the base layer 26 and extend away from a base plane which is generally defined by the base layer. The first mechanical fastening hook elements are configured to operably engage a selected, cooperating second mechanical fastening component, such as a conventional loop material. The medial section 28 of the first mechanical fastening component web can have a relatively lower density of the first mechanical fastening components elements per unit area, as compared to the side sections 30 and 32. The web of the first mechanical fastening component has extending sections of the carrier web material, such as carrier web sections 38 and 40, attached to extend laterally outboard from each of the side sections 30 and 32 of the first mechanical fastening component web. In particular, carrier web section 38 extends laterally outboard from the fastening side section 30, and carrier web section 40 extends laterally outboard from the fastening side section 32. At least the web of the first mechanical fastening component is divided along a serpentine division line 62 which extends generally longitudinally along the web of hook material 24.

In particular aspects of the invention, each section 38 and 40 of the carrier web material can have an extending web of panel material 56 attached to extend laterally outboard from each of the sections of carrier web material. In other aspects, the composite web 22 can be selectively segmented along segmenting lines 64 to provide the plurality of fastener components 66.

With respect to the shown arrangement, the first mechanical fastening component provides hook elements 54 which are configured to operably engage the selected, cooperating second mechanical fastening component provided by an operable loop material. The medial section 28 of the hook material web 24 can have a relatively lower density of the hook elements 54 per unit area, as compared to the side sections 30 and 32. The hook material web has extending sections of carrier web material, such as sections 38 and 40, one of which is attached to extend laterally outboard from each of the side sections 30 and 32 of the web of hook material 24. At least the web of hook material 24 is divided along the serpentine division line 62 which extends generally longitudinally along the web of hook material 24. It should be readily appreciated, however, that the loop material may be employed as the first mechanical fastening component and that the first mechanical fastening elements may be provided by loop elements. In a corresponding, complementary fashion, the hook material may be employed as the second mechanical fastening component.

In the shown arrangement, the method is arranged to provide a composite web 22 having an extending panel web 56 constructed of an elastomerically stretchable panel material attached to extend laterally outboard from each of the sections 38 and 40 of the carrier web material 34.

The shown arrangement of the method and apparatus also incorporates a single carrier web onto a surface of which a hook material web 24 is laminated and secured. As a result, the serpentine division line 62 operably divides both the hook material 24 and the carrier material web 34. Alternatively, the hook material web 24 may be positioned in-between a pair of laterally spaced apart carrier webs 34, and operably laminated and secured to the carrier webs. Accordingly, each of the individual carrier webs has first and second, laterally opposed side regions thereof. The first side region of each carrier web is attached to the web of hook material 24, and the second side region of each carrier web is operably attached to the outboard edge portion of its correspondingly associated side panel web 56.

The representatively shown method and apparatus generally has a longitudinal, machine-direction 86 and a lateral, cross-direction 88. At any particular, selected location along the method and apparatus, the machine-direction is the generally length-wise direction along which a particular web (or composite web) of material is moving or transported through the process. The cross-direction extends generally along the plane of the web of material, and is perpendicular to the particular machine-direction established by the method or apparatus at the selected location.

During the process of assembling the various described components, particular attaching or bonding mechanisms may be mentioned. It should be readily appreciated, however, many alternative mechanisms may also be employed. Such alternative techniques include, for example, ultrasonic bonding, thermal bonding, adhesive bonding, pressure bonding, laser bonding, microwave bonding and the like, as well as combinations thereof.

With regard to the shown configuration, the method for forming a plurality of fastener components includes providing a substantially continuous web of hook material along a selected longitudinal dimension 86. The hook material includes a hook base layer 26 which has a longitudinally extending medial section 28 located between first and second, laterally opposed, longitudinally extending side sections 30 and 32 of the web of hook material. The side sections are configured with mechanical fastening elements to provide first and second primary fastening sections of the web 24. In the representativley shown arrangements, each of the side sections 30 and 32 has a plurality of hook elements 54 which are integrally formed with the base layer 26 and extend away from a base plane which is generally defined by the hook base layer 26. The hook elements 54 are configured to operably engage a selected, cooperating loop material, such as loop material composed of an operative woven, nonwoven or knitted fabric. The medial section 28 has a relatively lower density of the hook elements 54 per unit area, as compared to the side sections 30 and 32. At least one substantially continuous web 34 of carrier material is attached to the web of hook material 24 to provide for an extending section of carrier web material which extends laterally outboard from each of the side sections 30 and 32 of the hook material web 24. A substantially continuous web of panel material 56 is attached to extend laterally outboard from each extending section of carrier web material, thereby forming a composite fastener web 22. At least the web of hook material 24 is divided along a serpentine division line 62 which extends generally longitudinally along the web of hook material 24. The serpentine line 62 has generally longitudinally extending portions 61 and generally laterally extending portions 63 (FIG. 3). The composite fastener web 22 is selectively segmented to provide for the plurality of fastener components 66.

With reference to FIGS. 1, 2, 3 and 4, a supplying means, such as supply roll 57, provides a first, panel web 56 composed of a selected panel material. The panel material may be substantially nonelastomeric or may be elastomeric. In particular configurations of the invention, the side panel material is composed of an elastomeric material which is elastically stretchable at least along the cross-direction 88 of the panel web 56. The panel material can, for example, be a stretch-bonded-laminate (SBL) material, a neck-bonded-laminate (NBL) material, an elastomeric film, an elastomeric foam material, or the like. For example, suitable meltblown elastomeric fibrous webs for forming panel web 56 are described in U.S. Pat. No. 4,663,220 issued May 5, 1987 to T. Wisneski et al., the entire disclosure of which is hereby incorporated by reference. Examples of composite fabrics comprising at least one layer of nonwoven textile fabric secured to a fibrous elastic layer are described in European Patent Application EP No. 0 110 010 published on Apr. 8, 1987 as EP 0 217 032 A2, with the inventors listed as J. Taylor et al., the entire disclosure of which is hereby incorporated by reference. Examples of NBL materials are described in U.S. Pat. No. 5,226,992 issued Jul. 13, 1993 to M. Mormon, the entire disclosure of which is hereby incorporated by reference. A particular neck-bonded-laminate (NBL) can be composed of a film of elastomer material sandwiched between two layers of spunbond material. The film can be composed of a KRATON® elastomer available from Shell Oil Company, and the spunbond layers can be composed of spunbond, polypropylene fibers.

A suitable separating mechanism, such as a slitter or other cutter 52, is employed to divide the panel web 56 into a first panel web section 74 and a second panel web section 76. In the illustrated configuration, for example, slitter 52 can separate the panel web 56 into first and second sections which have substantially equal cross-directional widths. Optionally, the separated web sections 74 and 76 can have unequal cross-directional widths, as desired. Each of the panel web sections has an inboard side edge region 58 and an outboard side edge region 60

The relative positioning of the first and second web sections 74 and 76, respectively, is adjusted to a desired spacing along the cross-deckle direction 88 of the process by an operable directing means, such as provided by a spreader mechanism 78. In the illustrated embodiment, for example, the spreader mechanism can include a conventional system of turn bars which reposition and relocate the first and second webs of side panel material at a desired spacing therebetween. For example, the spreader mechanism 78 can include a first pair of turn bars which are tilted and canted in a manner well known to the art to produce the desired repositioning of the first panel web section 74. The first panel web section 74 moves in an S-shaped path to pass over its first, top turn bar and then pass back and under its second, bottom turn bar to become offset by a predetermined distance away from second panel web section 76.

Similarly, a conventional second set of turn bars can be tilted and canted at appropriate angles in a manner well known in the art to selectively reposition the second panel web section 76. In particular, the second panel web section can be moved in another S-shaped path to pass over its first, top turn bar and then pass back and under its second, bottom turn bar in a manner which directs the second panel web section 76 to a position that is spaced the desired distance away from first panel web section 74.

Alternative spreader mechanisms include, for example, conventional guiding roller systems, such as those distributed by FIFE Corporation, a business having offices located in Oklahoma City, Oklahoma; and bowed rotating rolls, such as those distributed by Mt. Hope Machine Co., a business having offices in Taunton, Mass. Examples of other spreader mechanisms include non-parallel systems of rollers or bars, bowed non-rotating bars, grooved spreader rollers, crowned rollers and the like.

After the spreader mechanism has generated the desired lateral, cross-directional spacing between the first panel web section 74 and the second panel web section 76, the two panel web sections are directed to a second assembling means, such as provided by a system of assembly rollers 50.

A second supplying means, such as supply roll 23, supplies a web of the selected, first mechanical fastening component, such as the illustrated web 24 of hook material. The hook material web includes a base layer 26, and defines a first side section 30, a second side section 32, and a medial section 28 which is interposed between the first and second side sections of the hook material web. In addition, the base layer 26 has a first surface 46 and an oppositely located second surface 48. The first surface 46 is typically appointed to be inwardly facing of the associated article, and includes a plurality of fastening elements projecting and extending therefrom. The shown arrangement of the supply roll 23 has the hook elements extending radially outwardly from the supply roll. In particular aspects of the invention, the fastening elements are integrally formed with the base layer 26 and can be composed of substantially the same material as the base layer. Desired configurations include hook elements which are coextruded or otherwise integrally formed from the base layer material.

In the various arrangements of the invention, the medial section 28 can be substantially free of mechanical fastening elements. In particular configurations, the medial section can include selectively constructed protrusions (not shown) to improve the flexibility and/or tear resistance of the web of material which appointed to provide the first mechanical fastening component.

In particular aspects of the invention, the web of hook material 24 can be of the type referred to as micro-hook material. A suitable micro-hook material is distributed under the designation CS200 and is available from 3M Company, a business having offices in St. Paul, Minn. The micro-hook material can have hooks in the shape of mushroom "caps", and can be configured with a hook density of about 1600 hooks per square inch; a hook height which is within the range of about 0.033–0.097 cm (about 0.013 to 0.038 inch); and a cap width which is within the range of about 0.025–0.033 cm (about 0.01 to 0.013 inch). The hooks are attached to a base film substrate having a thickness of about 0.0076–0.01 cm (about 0.003–0.004 inch) and a Gurley stiffness of about 15 mg.

Another suitable micro-hook material is distributed under the designation VELCRO CFM-29 1058, and is available from VELCRO U.S.A., Inc., a business having offices in Manchester, N.H. The micro-hook material can have hooks in the shape of angled hook elements, and can be configured with a hook density of about 264 hooks per square centimeter (about 1700 hooks per square inch); a hook height which is within the range of about 0.030–0.063 cm (about 0.012–0.025 inch); and a hook width which is within the range of about 0.007 to 0.022 cm (about 0.003 to 0.009 inch). The hook elements are coextruded with a base layer substrate having a thickness of about 0.0076–0.008 cm (about 0.003–0.0035 inch) and the member of hook material has a Gurley stiffness of about 12 mg.

In the shown configuration, the medial section of the web of hook material 24 is substantially free of hook elements 54. In other aspects of the invention, the average hook element density (frequency of occurrence) per unit area of the medial section 28 can be not more than about 75 percent (%) of the average hook element density within the primary fastening, side sections 30 and 32. Alternatively, the hook element density in the medial section 28 can be not more than about 70%, and optionally can be not more than about 60% of the hook element density within its adjacently located fastening sections 30 and 32 of the hook material web 24 to provide desired characteristics. In further aspects, the average hook element density per unit area of the grip region 52 can be not less than about 25% of the average hook element density within the primary fastening, side sections 30 and 32. Alternatively, the hook element density in the grip region 52 can be not less than about 30%, and optionally can be not less than about 40% of the hook element density within its adjacently located fastening sections 30 and 32 of the hook material web 24 to provide improved performance. The average hook element density can, for example, be adjusted by increasing or decreasing the spacing between individual hook elements. Alternatively, the average hook element density can be adjusted by limiting the placement of the hook elements into localized areas to create a selected patchwork pattern of segregated, "island" areas which contain the hook elements. The island areas are distributed within a "sea" area that is substantially devoid of operable hook elements.

Figure 5:
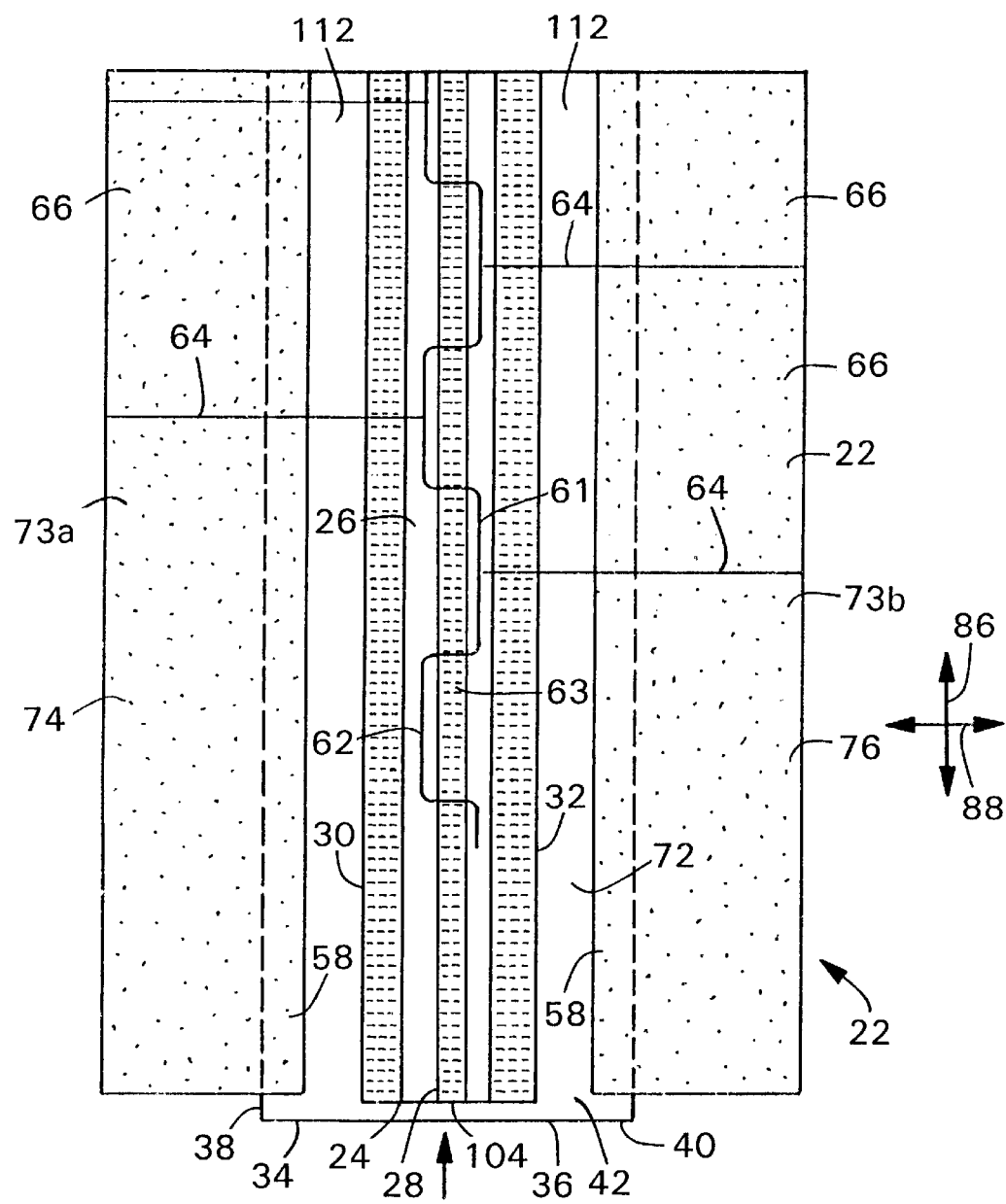
FIG. 5 representatively shows another schematic composite web and its associated components.
Figure 6:
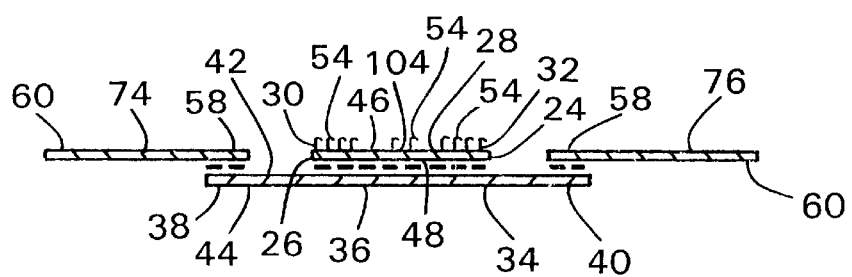
FIG. 6 representatively shows an expanded, schematic cross-sectional, lateral end view of the composite web illustrated in FIG. 5.

With reference to FIGS. 5 and 6, the web of hook material 24 can be configured with a longitudinally extending supplemental fastening region 104, which in the shown arrangement, is positioned substantially along the longitudinal centerline of the web 24. The supplemental fastening region provides for a relatively lower, total fastening strength, as compared to the primary fastening sections provided at the side sections 30 and 32 of the base layer 26. The lower fastening strength can, for example, be provided for by reducing the effective area of the selected fastening component positioned in the supplemental fastening region, or by reducing the area density of the selected fastening elements located in the supplemental fastening region. In particular aspects, the supplemental fastening region 104 can be configured substantially coterminous with either or both of the longitudinally extending portions 61 and the laterally extending portions 63 of the serpentine division line 62. In other aspects, the supplemental fastening region 104 can be configured spaced away from at least the longitudinally extending portions 61 of the serpentine division line by a selected spacing distance.

With reference again to FIGS. 1, 2 and 3, at least one carrier web 34 is delivered from a suitable source, such as supply roll 35. In particular configurations of the invention, the material of carrier layer 56 can be composed of a substantially non-elastomeric material, such as polymer films, woven fabrics, nonwoven fabrics or the like, as well as combinations thereof. Alternatively, the carrier web material may be composed of a substantially elastomeric material, such as a stretch-bonded-laminate (SBL) material, a neck-bonded-laminate (NBL) material, an elastomeric film, an elastomeric foam material, or the like, as well as combinations thereof. The elastomeric material is elastomerically stretchable at least along the lateral dimension 88. For example, the carrier web material may be composed of a spunbond-meltblown-spunbond (SMS) fabric having a core of meltblown fibers sandwiched between two facing layers of spunbond fibers to provide a total composite basis weight within the range of about 50–67 g/m$^2$ (about 1.5–2 oz/yd$^2$). As another example, the carrier web material may be entirely composed of a nonwoven spunbond fabric having a basis weight within the range of about 50–67 g/m$^2$ (about 1.5–2 oz/yd$^2$).

As representatively shown, the carrier web 34 has a first major facing surface 42 and a second major facing surface 44. The carrier web also has a first side section 38, a second side section 40, and a medial section 36 which is interposed between the first and second side sections of the carrier web, and is positioned generally along a longitudinal centerline of the carrier web. The second surface 48 of the web of hook material 24 is operably bonded and laminated to the medial portion 36 of the first surface 42 of the carrier web to provide a composite fastener web 72. An operative attaching mechanism, such as the shown adhesive applicator 82, generates an attachment for operably affixing the hook material web 24 to the associated carrier web 34, and a conventional assembly mechanism, such as a system of rollers 84, mount the hook material onto the carrier web. The applicator can be configured to generate any conventional arrangement of adhesive, such as a slot coating, a bead, a spray, a swirl pattern or the like, as well as combinations thereof. Desirably, the hook material web is substantially centered along the cross-direction of the carrier web 34. The resultant assembly provides a composite web laminate in which the hook elements 54 are in a generally exposed position. The composite fastener web 72 can then be operably directed and transported for further processing.

In the representatively shown configuration of the invention, suitable directing means, such as a conventional system of guiding rollers (not shown), transport the fastener web 72 to a position which is interposed between the panel web sections 74 and 76. A suitable attaching mechanism, such as the shown system of adhesive applicator 90 and ultrasonic bonder 92, generates an attachment for affixing the composite fastener web 72 in between the laterally spaced-apart, panel web sections 74 and 76 to provide the composite web 22. More particularly, the adhesive applicator initially attaches outboard edges of the composite web 72 to associated, overlapping edges of each of the panel web sections 74 and 76. The inboard edge region 58 of the first panel web section 74 attaches to the overlapping first side edge region 39 of the first side section 38 of the carrier web 34, and the inboard edge region 58 of the second panel web section 76 attaches to the overlapping second side edge region 41 of the second side section 40 of the carrier web. The shown arrangements laminate the panel webs onto the first surface 42 of the carrier web 34. Alternatively, the panel webs may be laminated onto the opposite, second surface 44 of the carrier web. The sonic bonder can desirably be employed to supplement the initial attachments with sonic, thermal bonds. The sonic bonder can also generate an attachment between the hook material 24 and the carrier web 34, which together have provided the composite web 72.

The composite web can then be moved or otherwise directed for further processing. For example, the composite web 22 may be wound onto rolls, such as storage rolls 124, or otherwise configured for transport to another, remotely located manufacturing line which is employed to produce garments or other desired articles. Alternatively, the composite base web 22 can be operably delivered directly into subsequent stages of a manufacturing line along a connecting path A.

With reference to FIG. 2, the composite base web 22 can be operably delivered into a second separating means, such as a die cutting system 94 or the like, to longitudinally divide the composite web into a pair of composite fastener web sections 73a and 73b. The cutter can produce a periodic, substantially regularly undulating, serpentine division line 62 which is positioned along a medial section of the composite base web 22. The serpentine line extends generally along the machine-direction, longitudinal length dimension of the composite web 22 and includes alternately traversing, side-to-side sections thereof. The traversing sections of the division line can optionally include retroceding portions thereof to provide for distinctively shaped fastening tabs 112. The division line 62 separates apart at least the web of hook material 24. In the shown configurations, the division line separates apart both the web of hook material and the web of carrier material 34. In addition, the traversing sections of the serpentine line are selectively arranged to substantially avoid extending into the distributions of hook elements 54 located in the first and second side regions 30 and 32 of the hook material web 24. Additional details regarding the construction of suitable fastening tabs and fastening systems are, for example, described in the previously mentioned U.S. patent application Ser. No. 168,615 of T. Roessler et al., entitled DYNAMIC FITTING DIAPER, filed Dec. 16, 1993 (attorney docket No. 10,961); and U.S. patent application Ser. No. 603,477 of A. Long et al., entitled MECHANICAL FASTENING SYSTEM WITH GRIP TAB, filed Mar. 6, 1996 (attorney docket No. 12,563).

In the shown configuration of the invention, the composite fastener web sections 73a and 73b are operably directed to a system of conventional folding boards 76 to reposition the individual fastening tabs 112 into a storage position against an appointed surface of its associated fastener web section 73a or 73b, as desired.

A phase adjusting means, such as provided by alignment turn bars 116 and 118, operably everts the fastener webs 73a and 73b, and repositions the lengthwise, machine-directional phasing of the fastener tabs on first fastener web section 73a relative to the fastener tabs on second fastener web section 73b. In the everting operation, the fastener web sections 73a and 73b are laterally flipped and reversed such that the fastening tabs 112 are shifted from being located along the inboard edge regions of the fastener webs, and are moved to become located along the outboard edge regions of the fastener webs. The additional repositioning, phasing operation is configured to operably arrange appointed, corresponding pairs of fastening tabs 112 into a substantial cross-deckle alignment along the cross-direction of the process and apparatus. Accordingly, the process and apparatus provide at least one corresponding, laterally opposed pair of fasteners, which includes a first fastener tab from the first composite fastener web section 73a and a second fastener tab from the second composite fastener web 73b. In the illustrated embodiment, the process is advantageously constructed to provide a serial multiplicity of corresponding, laterally opposed pairs of the first and second fasteners.

The substantially aligned first and second fastener web sections 73a and 73b can be prepared for further attachment to other components of the desired article. In the illustrated configuration, for example, the composite fastener web sections 73a and 73b are directed to an applicator 120 which deposits a suitable adhesive onto the regions of the composite fastener web sections that are appointed for further attachment. Other attaching mechanisms, such as thermal bonds, sonic bonds and the like may also be employed to supplement or replace the described adhesive attachment.

In further aspects of the method and apparatus of the invention, the first and second fastener web sections 73a and 73b are directed to a suitable third separating mechanism, such as a system of rotary cutters 96, for partitioning along the cross-direction of the fastener web sections to form a plurality of individual fastener components 66. The individual fastener systems are directed to a suitable construction assembling mechanism, such as a system of assembly rollers, which can be configured to attach individual fastener systems onto a major body-facing side or outward-facing side of an article web 68, as desired.

For example, a phased, cut-and-place, intermittent assembling means, such as a mechanism comprising a system of conventional vacuum slip rolls 110 and a rotary knife and anvil systems 96, can be employed to connect opposed, cross-directionally aligned pairs of the fastener components 66 to laterally opposite side regions 98 of the article web 68. In the illustrated embodiment, for example, the cut-and-place assembling mechanism is constructed and arranged to operably connect a sequential plurality of the paired fastener components 66 to the article web at a plurality of predetermined, spaced-apart locations along the machine-direction of the article web 68. An example of a suitable arrangement of rotary cutter and vacuum slip roll is described in U.S. Pat. No. 4,795,51 0 issued Jan. 3, 1989 to M. Wittrock et al. and entitled "PROCESS FOR APPLYING REINFORCING MATERIAL TO A DIAPER COVER MATERIAL" (attorney docket No. 8366), the disclosure of which is hereby incorporated by reference in a manner that is consistent herewith.

The assembly mechanism operatively affixes the individual fastener components 66 to the opposed sides 98 of the article web 68, and opposed pairs of the individual fastener components 66 are substantially aligned along the cross-direction 88 of the article web 68. In addition, ultrasonic bonders 126 may be employed to provide additional securement between the fastener components 66 and the article web 68. The article web can then be further processed and separated into a plurality of individual articles by conventional separating means.

In particular, the resultant article web 68 can be constructed to define an interconnected plurality of individual article segments 122, and a conventional cutting mechanism (not shown) can then separate the article web 68 along preselected division lines 100 to produce selected individual articles. The separating step can be performed by employing any conventional cutting mechanism, such as a rotary cutter or the like.

The invention can further include mechanisms for providing a web of backsheet material, and for positioning at least one absorbent body at a selected location along a machine directional length of the backsheet web. A plurality of absorbent bodies can, for example, be positioned at predetermined, regularly spaced locations along the length of the backsheet web. Another mechanism can then deliver a web of topsheet material to sandwich the absorbent body between the web of backsheet material and the web of topsheet material.

Other aspects of the invention can include a mechanism for attaching at least a pair of lengthwise extending elasticized containment flaps to the bodyside surface of the topsheet web. Suitable containment flap configurations are described in detail in U.S. Pat. No. 4,704,116 issued Nov. 11, 1987 to K. Enloe and entitled DIAPERS WITH ELASTICIZED SIDE POCKET, the disclosure of which is hereby incorporated by reference in a manner that is consistent herewith. Other containment flap configurations are described in U.S. patent application Ser. No. 206,816 of R. Everett et al., entitled ABSORBENT ARTICLE HAVING AN IMPROVED SURGE MANAGEMENT and filed Mar. 4, 1994 (attorney docket No. 11,375), the disclosure of which is hereby incorporated by reference in a manner that is consistent herewith.

Figure 7:
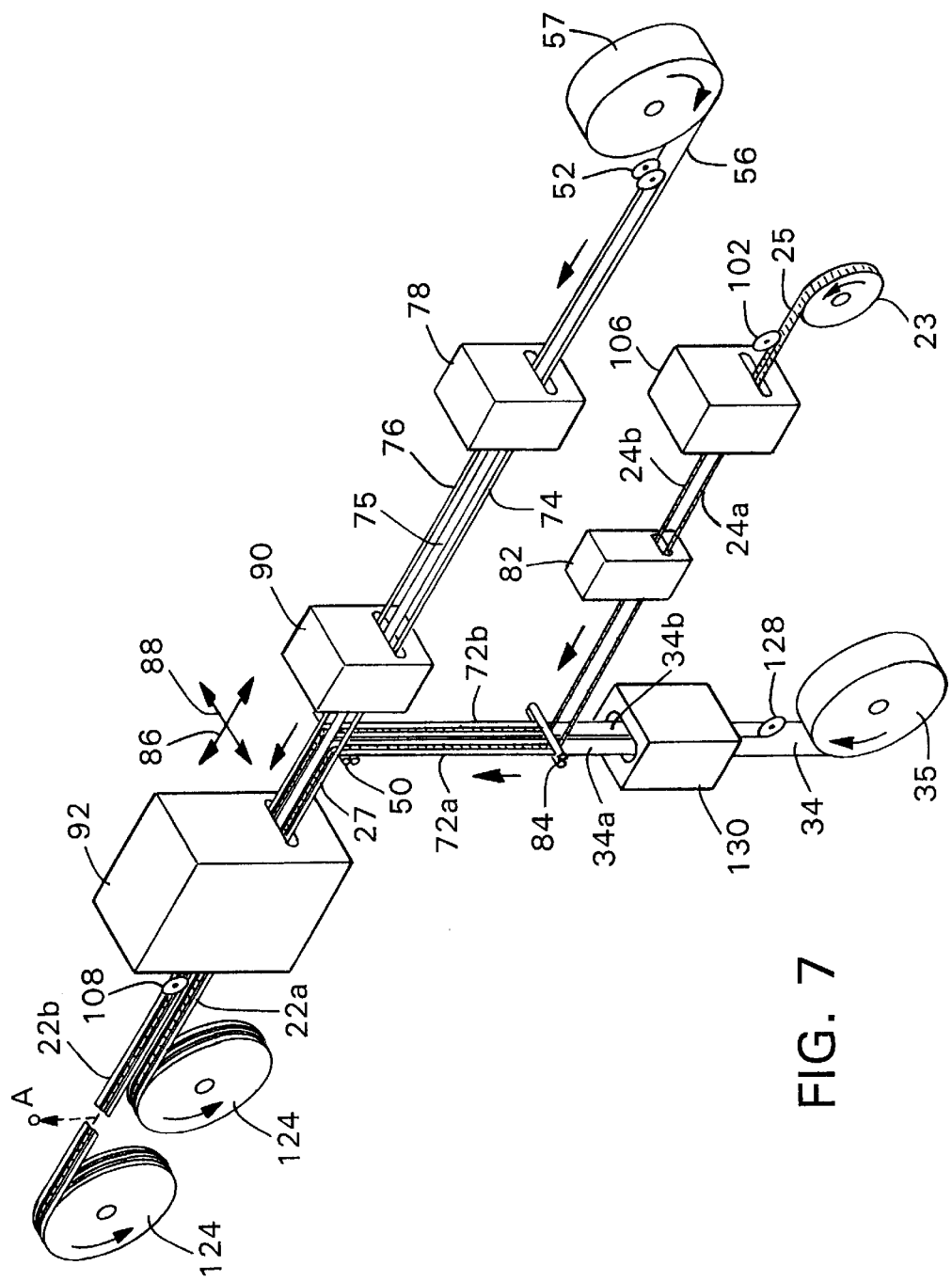
FIG. 7 representatively shows an alternative configuration of the method and apparatus of the invention for making multiple composite webs.
Figure 10:
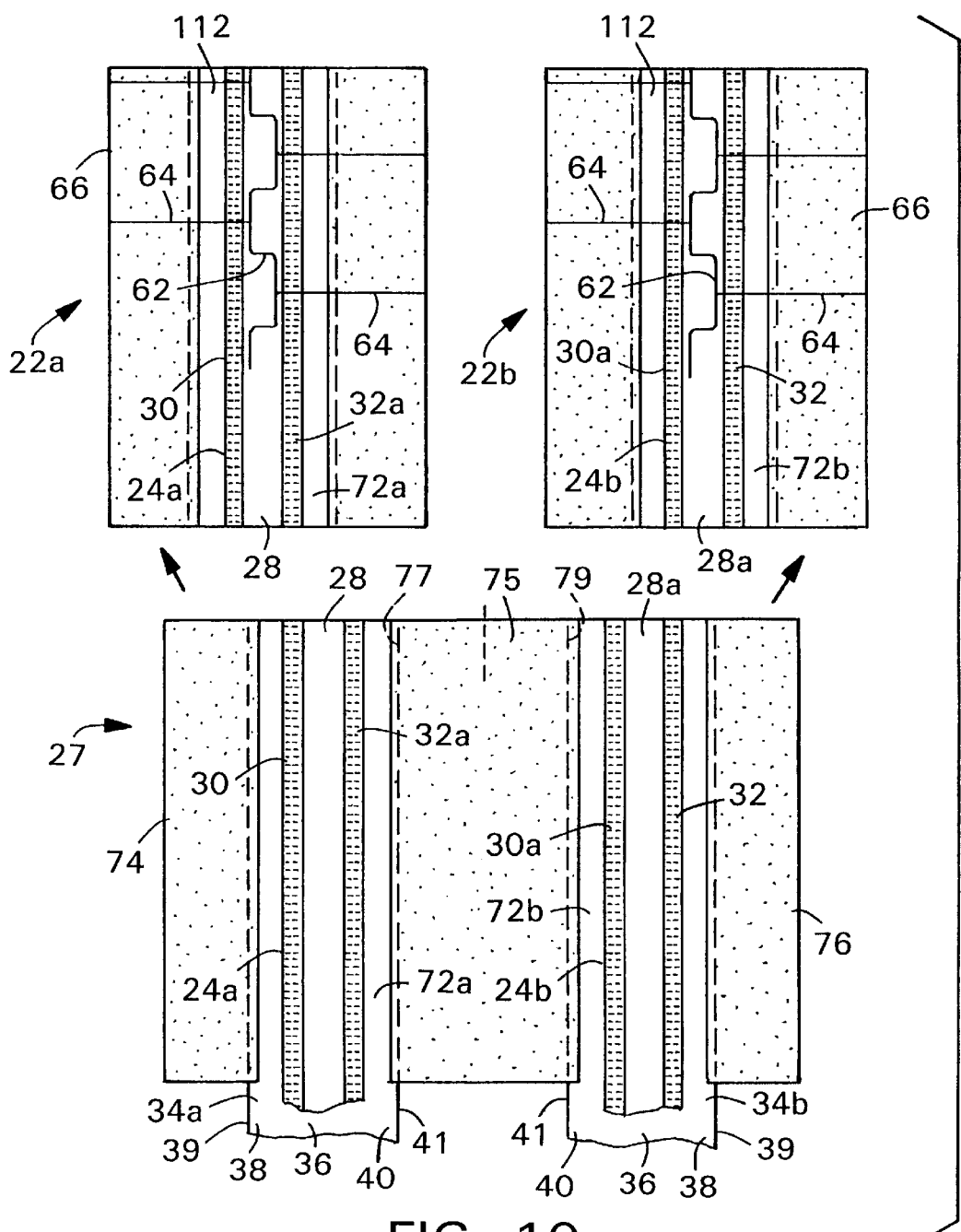
FIG. 10 representatively shows a further, schematic composite web assembly and its associated components.
Figure 11:
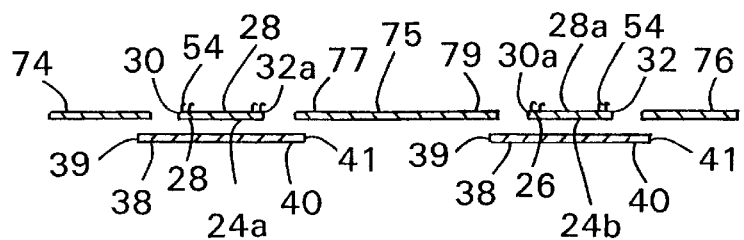
FIG. 11 representatively shows an expanded, schematic cross-sectional, lateral end view of the composite web assembly illustrated in FIG. 10.

With reference to FIGS. 7, 10 and 11, another aspect of the invention can provide a system for producing a set of multiple composite webs 22. The shown method and apparatus for forming fastener components, is configured to provide first and second substantially continuous webs of a first mechanical fastening component, such as webs of hook material 24a and 24b. Each of the first mechanical fastening components includes a base layer, such as hook base layer 26, which has a longitudinally extending medial section, such as medial section 28 or 28a, located between first and second, laterally opposed, longitudinally extending side sections, such as side edge regions, such as side sections 30 and 32a or side sections 30a and 32, of the web of the first mechanical fastening component. Each of the side sections has a plurality of first mechanical fastening elements, such the shown hook elements 54, which are integrally formed with said base layer and extend away from a base plane of the hook base layer. The first mechanical fastening elements are configured to operably engage a selected, cooperating second mechanical fastening component, such as a loop material. The medial section can have a relatively lower density of said first mechanical fastening elements per unit area, as compared to said side sections. Optionally, the medial section of any of the webs 24 can be substantially free of operable hook elements or other mechanical fastening elements. At least one, substantially continuous web of carrier material, such as a carrier web 34a or 34b, is attached to each of said first and second webs of the first mechanical fastening component. Each of the at least one web of carrier material provides for an extending section of carrier web material, such as carrier side section 38 or 40, which extends laterally away from each of the side sections of each of said first and second webs of said first mechanical fastening component. In addition, each of the at least one web of carrier material provides an appointed first carrier side edge region, such as a side edge portion 39 of carrier side section 38, and an appointed second carrier side edge region, such as a side edge portion 41 of carrier side section 40. A substantially continuous, relatively central web of panel material, such as panel web 75, is attached to the second side edge portion 41 of each of the at least one web of carrier material, and a relatively outboard web of panel material, such as provided by panel web 74 or 76, is attached to extend laterally outboard from the first side edge portion 39 of each of the at least one web of carrier material, thereby forming a composite fastener web assembly 27.

In particular aspects, the technique of the invention can further include a dividing of the relatively central web 75 of panel material to provide first and second composite fastener webs, such as composite webs 22a and 22b. In other aspects, the technique of the invention can include a dividing of at least the web of the first mechanical fastening component, such as web 24a and/or 24b, within at least one of the composite fastener webs along a serpentine division line 62 which extends generally longitudinally along the web of hook material.

The representatively shown configuration includes a supplying means, such as supply roll 57, which provides a first, panel web 56 composed of the selected panel material. The panel material may be substantially nonelastomeric or may be elastomeric, as previously described.

A suitable separating mechanism, such as a system of slitters 52 or other cutters, is employed to divide the panel web 56 into a plurality of sections. For example, the panel web 56 can be separated into the first panel web section 74, the second panel web section 76, and at least a third panel web section 75. In the illustrated configuration, for example, slitter 52 can partition the panel web 56 into three sections, wherein the first and second sections have substantially equal cross-directional widths, and the third section 75 has a cross-directional width which is approximately twice as large as that of the first and second sections. Optionally, any or all of the separated web sections 74, 75 and 76 can have relatively equal or unequal cross-directional widths, as desired. Each of the panel web sections 74 and 76 has an inboard side edge region 58 and an outboard side edge region 60. The third, relatively middle web section 75 has first and second side edge regions 77 and 79, respectively.

The relative lateral positionings of the first, second and third web sections 74, 75 and 76, respectively, are desirably adjusted to a desired spacing along the cross-deckle direction 88 of the process by an operable directing means, such as provided by the spreader mechanism 78. In the illustrated embodiment, for example, the spreader mechanism can include a conventional guiding system which repositions and relocates each of the first and second webs of side panel material at a desired spacing away from the third web 75 of side panel material. For example, the spreader 78 can include any of the conventional spreader mechanisms described herein. After the spreader mechanism has generated the desired lateral, cross-directional spacings of the first and second panel web sections away from the relatively centrally located, third panel web section 75, the three panel web sections are directed to a second assembling means, such as provided by the system of assembly rollers 50.

Figure 8:
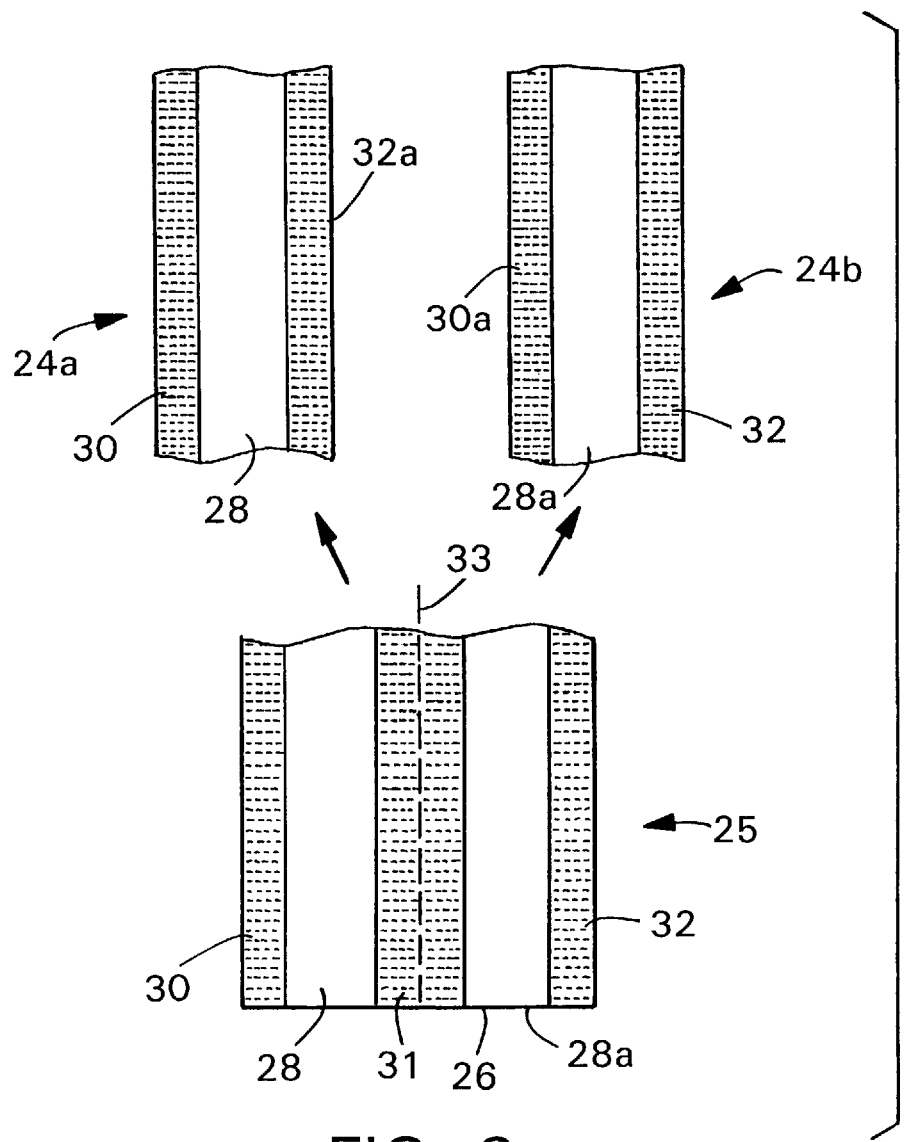
FIG. 8 representatively shows an alternative web of hook material.
Figure 9:
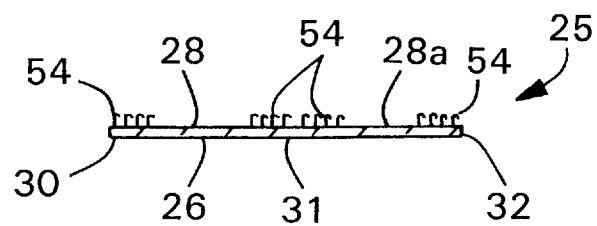
FIG. 9 representatively shows an expanded, schematic cross-sectional, lateral end view of the hook material web illustrated in FIG. 8.

With reference to FIGS. 7, 8 and 9, a second supplying means, such as supply roll 23, supplies a web of the selected, first mechanical fastening component, such as the illustrated web 25 of hook material. The hook material web includes a base layer 26, and defines a first side section 30, a second side section 32, a generally central section 31, and a pair of laterally spaced-apart medial sections 28 and 28a. The medial section 28 is juxtaposed between the first side section 30 and the central section 31 of the hook material web, and the medial section 28a is juxtaposed between the second side section 32 and the central section 31 of the hook material web. As previously mentioned, the base layer 26 has a first surface 46 and an oppositely located second surface 48. The first surface 46 is typically appointed to be inwardly facing of the associated article, and includes a plurality of fastening elements projecting and extending therefrom. The shown arrangement of the supply roll 23 has the hook elements extending radially outwardly from the supply roll. In particular aspects of the invention, the fastening elements are integrally formed with the base layer 26 and can be composed of substantially the same material as the base layer. Desired configurations include hook elements which are coextruded or otherwise integrally formed from the base layer material.

The shown configuration of the invention delivers the hook material web 25 to a suitable dividing mechanism, such as the shown slitter 102, which separates the web 25 into a set of two discrete webs 24a and 24b. The shown slitter cuts along a longitudinal centerline of the central section 31 of the hook material web to provide sections 30a and 32a, as desired for the intended configurations of the webs 24a and 24b. Alternatively, the central section 31 of the web 25 may include a constructed line of weakness which extends longitudinally along the web. The line of weakness is constructed to allow the web 25 to be selectively and reliably fractured or torn along an appointed separation line 33. The shown webs 24a and 24b are substantially identical to each other. Optionally, however, the slitter can be configured and arranged to provide webs 24a and 24b which differ from each other. After the dividing operation, the web set composed of webs 24a and 24b are directed through a conventional spreader mechanism 106 which operatively positions the webs in a desired, laterally spaced-apart configuration, as appropriate for subsequent processing operations.

With reference again to FIGS. 7, 10 and 11, at least one carrier web 34 is delivered from a suitable source, such as supply roll 35. In the shown arrangement, the carrier web 34 is divided into a set of two carrier webs 34a and 34b by a slitter 128 or other suitable separating mechanism, and the carrier webs are positioned in a desired, laterally spaced-apart relationship by a suitable spreader device 130. Optionally, the set of carrier webs can be delivered from separate supply rolls. As representatively shown, each of the carrier webs 34a and 34b has a first major facing surface 42 and a second major facing surface 44. Each carrier web also provides for a first side section 38, a second side section 40, and a medial section 36 which is interposed between the first and second side sections of the carrier web and is positioned generally along a longitudinal centerline of the carrier web. The second surface 48 of the web 24a of hook material is operably bonded and laminated to the medial portion 36 of the first surface 42 of carrier web to 34a provide a first composite fastener web 72a, and the surface 48 of the web 24b of hook material is operably bonded and laminated to the medial portion 36 of the first surface 42 of carrier web to 34b provide a second composite fastener web 72b. An operative attaching mechanism, such as the shown adhesive applicator 82, generates an attachment for operably affixing each of the hook material webs 24a and 24b to its associated carrier web 34a and 34b. Desirably, each hook material web is substantially centered along the cross-direction of its corresponding carrier web 34. The resultant assemblies provides a set of two composite web laminates in which the hook elements 54 are in a generally exposed position. The assembled composite fastener webs 72a and 72b can then be operably directed and transported for further processing.

In the representatively shown configuration of the invention, suitable directing means, such as the shown system of guiding rollers 84 and 50, transport the fastener webs 72a and 72b to positions which are operatively interposed between the panel web sections 74, 75 and 76. In particular, fastener web 72a is located to extend and span between panel web sections 74 and 75, and fastener web 72b is located to extend and span between panel web sections 75 and 76. A suitable attaching mechanism, such as the shown system of adhesive applicator 90 and ultrasonic bonder 92, generates an attachment for affixing each of the composite fastener webs 72a and 72b in between its corresponding pair of laterally spaced-apart, panel web sections 74–75 and 76–75, respectively, to provide the composite fastener web assembly 27. More particularly, the adhesive applicator initially attaches the side edges of each of the composite webs 72a and 72b to corresponding, overlapping edges of its associated pair of panel web sections 74–75 and 76–75, respectively. The inboard edge region 58 of the first panel web section 74 attaches to the overlapping first side edge region 38 of the carrier web 34a, and the second side edge region 40 of the carrier web 34a attaches to the first, overlapping side edge region 77 of panel web 75. Similarly, the inboard edge region 58 of the second panel web section 76 attaches to the overlapping first side edge region 38 of the carrier web 34b, and the second side edge region 40 of the carrier web 34b attaches to the second, overlapping side edge region 79 of panel web 75. The sonic bonder 92 supplements the initial attachments with ultrasonic, thermal bonds. The sonic bonder can also be configured to generate an attachment between the hook materials 24a and 24b and the carrier webs 34a and 34b, which together have provided the composite webs 72a and 72b, respectively.

The composite web assembly 27 can then be moved or otherwise directed for further processing. For example, the composite web assembly 27 can be directed to another dividing mechanism, such as provided for by slitter 108, to separate the web assembly 27 into a set of two composite webs 22a and 22b. Each of the composite webs 22a and 22b may be wound onto rolls 124 or otherwise configured for transport to another, remotely located manufacturing line which is employed to produce garments or other desired articles. Alternatively, either or both of the composite base webs 22a and 22b can be operably delivered directly into subsequent stages of an associated manufacturing line (e.g. FIG. 2) along an individual connecting path A.

Having described the invention in rather full detail, it will be readily apparent that various changes and modifications can be made without departing from the spirit of the invention. All of such changes and modifications are contemplated as being within the scope of the invention as defined by the subjoined claims.

We claim:

1. A method for forming fastener components, comprising:

providing a composite web which includes a web of a first mechanical fastening component, said first mechanical fastening component web including a base layer which has a longitudinally extending medial section located between first and second, laterally opposed, longitudinally extending side sections of said first mechanical fastening component web, each of said side sections having a plurality of first mechanical fastening elements which are integrally formed with said base layer and extend away from a base plane of said base layer, said first mechanical fastening elements configured to operably engage a selected, cooperating second mechanical fastening component, said medial section having first mechanical fastening elements therein, said first mechanical fastening elements in said medial section arranged with a relatively lower density of said first mechanical fastening elements per unit area, as compared to said side sections, said web of said first mechanical fastening component having an extending section of carrier web material attached to extend laterally outboard from each of said side sections of said web of said first mechanical fastening component; and dividing at least said web of said first mechanical fastening component along a serpentine division line which extends generally longitudinally along said first mechanical fastening component web.

2. A method as recited in claim 1 further comprising a selective segmenting of said composite web to provide for said plurality of fastener components.

3. A method as recited in claim 1, wherein an extending web of panel material has been attached to extend laterally outboard from each section of carrier web material.

4. A method as recited in claim 1, wherein said first mechanical fastening component web is provided by a web of hook material, said first mechanical fastening elements are provided by hook elements and said second mechanical fastening component is provided by a loop material, said hook material web including a hook base layer which has a longitudinally extending medial section located between first and second, laterally opposed, longitudinally extending side sections of said web of hook material, each of said side sections having a plurality of said hook elements which are integrally formed with said hook base layer and extend away from a base plane of said hook base layer, said hook elements configured to operably engage said loop material, said medial section having hook elements therein, and said hook elements arranged with a relatively lower density of said hook elements per unit area, as compared to said side sections.

5. A method as recited in claim 4, wherein an extending web of panel material has been attached to extend laterally outboard from each section of carrier web material.

6. A method as recited in claim 1, wherein said method is arranged to provide a composite web having an extending panel web of elastomerically stretchable panel material attached to extend laterally outboard from each section of carrier web material.

7. A method as recited in claim 1, further comprising an attaching of said fastener components to appointed side regions of an article web.

8. A method as recited in claim 7, further comprising a sectioning of said article web into a plurality of individual articles.

9. A method as recited in claim 1, wherein said method provides said serpentine division line in a configuration which substantially avoids extending into said side sections of said web of said first mechanical fastening component.

10. A method for forming a plurality of fastener components, comprising:

providing a substantially continuous web of a first mechanical fastening component, said first mechanical fastening component including a base layer which has a longitudinally extending medial section located between first and second, laterally opposed, longitudinally extending side sections of said web of said first mechanical fastening component, each of said side sections having a plurality of first mechanical fastening elements which are integrally formed with said base layer and extend away from a base plane of said base layer, said first mechanical fastening elements configured to operably engage a selected, cooperating second mechanical fastening component, said medial section having first mechanical fastening elements therein, said first mechanical fastening elements in said medial section arranged with a relatively lower density of said first mechanical fastening elements per unit area, as compared to said side sections, attaching at least one, substantially continuous web of carrier material to said web of said first mechanical fastening component to provide for an extending section of carrier web material which extends laterally outboard from each of said side sections of said web of said first mechanical fastening component;

attaching a substantially continuous web of panel material to extend laterally outboard from said each extending section of carrier web material, thereby forming a composite fastener web; and dividing at least said web of said first mechanical fastening component along a serpentine division line which extends generally longitudinally along said medial section of said web of said first mechanical fastening component.

11. A method for forming a plurality of fastener components, comprising providing a substantially continuous web of hook material, said hook material including a hook base layer which has a longitudinally extending medial section located between first and second, laterally opposed, longitudinally extending side sections of said web of hook material, each of said side sections having a plurality of hook elements which are integrally formed with said base layer and extend away from a base plane of said hook base layer, said hook elements configured to operably engage a selected, cooperating loop material, said medial section having hook elements therein, said hook elements in said medial section arranged with a relatively lower density of said hook elements per unit area, as compared to said side sections;

attaching at least one, substantially continuous web of carrier material to said web of hook material to provide for an extending section of carrier web material which extends laterally outboard from each of said side sections of said web of hook material;

attaching a substantially continuous web of panel material to extend laterally outboard from said each extending section of carrier web material, thereby forming a composite fastener web; and dividing at least said web of hook material along a serpentine division line which extends generally longitudinally along said medial section of said web of hook material.

12. A method as recited in claim 10, wherein said method is arranged to attach a substantially continuous web of elastomerically stretchable panel material to extend laterally outboard from said each extending section of carrier web material, thereby forming said composite fastener web.

13. A method as recited in claim 10, wherein said method is configured to provide first and second substantially continuous webs of carrier material which are operably attached to thereby provide said sections of carrier web material which extend laterally outboard from each of said side sections of said web of said first mechanical fastening component.

14. A method as recited in claim 10, wherein said method provides said serpentine division line in a configuration which substantially avoids extending into said side sections of said web of said first mechanical fastening component.

15. A method as recited in claim 10, further comprising an attaching of said fastener components to appointed side regions of an article web.

16. A method as recited in claim 15, further comprising a sectioning of said article web into a plurality of individual articles.

17. A method for forming fastener components, comprising:

providing first and second substantially continuous webs of a first mechanical fastening component, each web of said first mechanical fastening component including a base layer which has a longitudinally extending medial section located between first and second, laterally opposed, longitudinally extending side sections of said web of said first mechanical fastening component, each of said side sections having a plurality of first mechanical fastening elements which are integrally formed with said base layer and extend away from a base plane of said base layer, said first mechanical fastening elements configured to operably engage a selected, cooperating second mechanical fastening component, said medial section having first mechanical fastening elements therein, said first mechanical fastening elements in said medial section arranged with a relatively lower density of said first mechanical fastening elements per unit area, as compared to said side sections, attaching at least one, substantially continuous web of carrier material to each of said first and second webs of said first mechanical fastening component, each of said at least one web of carrier material providing for an extending section of said carrier web material which extends laterally away from each of said side sections of each of said first and second webs of said first mechanical fastening component, and each of said at least one web of carrier material providing an appointed first carrier side edge region and an appointed second carrier side edge region;

attaching a substantially continuous, relatively central web of panel material to said second side edge portion of each of said at least one web of carrier material; and attaching a relatively outboard web of panel material to extend laterally outboard from said first side edge portion of each of said at least one web of carrier material, thereby forming a composite fastener web assembly.

18. A method as recited in claim 17 further comprising a dividing of said relatively central web of panel material to provide first and second composite fastener webs.

19. A method as recited in claim 18 further comprising a dividing of at least one web of said first mechanical fastening component within at least one of said composite fastener webs along a serpentine division line which extends generally longitudinally along said medial section of said at least one web of said first mechanical fastening component.

20. A method for forming fastener components, comprising:

providing a composite web which includes a web of a first mechanical fastening component, said first mechanical fastening component web including a base layer which has a longitudinally extending medial section located between first and second, laterally opposed, longitudinally extending side sections of said first mechanical fastening component web, each of said side sections having a plurality of first mechanical fastening elements which are integrally formed with said base layer and extend away from a base plane of said base layer, said first mechanical fastening elements configured to operably engage a selected, cooperating second mechanical fastening component, said medial section having a supplemental fastening region with first mechanical fastening elements therein, said first mechanical fastening elements in said supplemental fastening region arranged to provide a relatively lower fastening strength, as compared to said side sections, said web of said first mechanical fastening component having an extending section of carrier web material attached to extend laterally outboard from each of said side sections of said web of said first mechanical fastening component; and dividing at least said web of said first mechanical fastening component along a serpentine division line which extends generally longitudinally along said medial section of said first mechanical fastening component web.

21. A method as recited in claim 20, wherein said first mechanical fastening component web is provided by a web of hook material, said first mechanical fastening elements are provided by hook elements and said second mechanical fastening component is provided by a loop material, said web of hook material including a hook base layer which has a longitudinally extending medial section located between first and second, laterally opposed, longitudinally extending side sections of said web of hook material, each of said side sections having a plurality of hook elements which are integrally formed with said base layer and extend away from a base plane of said hook base layer, said hook elements configured to operably engage said loop material, and said medial section having a supplemental fastening region with hook elements arranged to provide a relatively lower fastening strength, as compared to said side sections.

22. A method for forming fastener components, comprising:

providing a composite web which includes a web of a first mechanical fastening component, said first mechanical fastening component web including a base layer which has a longitudinally extending medial section located between first and second, laterally opposed, longitudinally extending side sections of said first mechanical fastening component web, each of said side sections having a plurality of first mechanical fastening elements which are integrally formed with said base layer and extend away from a base plane of said base layer, said first mechanical fastening elements configured to operably engage a selected, cooperating second mechanical fastening component, said medial section including selectively constructed protrusions therein for improving a flexibility of said first mechanical fastening component web, said web of said first mechanical fastening component having an extending section of carrier web material attached to extend laterally outboard from each of said side sections of said web of said first mechanical fastening component; and dividing at least said web of said first mechanical fastening component along a serpentine division line which extends generally longitudinally along said medial section of said first mechanical fastening component web.

23. A method as recited in claim 22, wherein said first mechanical fastening component web is provided by a web of hook material, said first mechanical fastening elements are provided by hook elements and said second mechanical fastening component is provided by a loop material, said hook material web including a hook base layer which has a longitudinally extending medial section located between first and second, laterally opposed, longitudinally extending side sections of said web of hook material, each of said side sections having a plurality of said hook elements which are integrally formed with said base layer and extend away from a base plane of said hook base layer, said hook elements configured to operably engage said loop material.

* * * * *